US008644905B2

(12) United States Patent
Kober et al.

(10) Patent No.: US 8,644,905 B2
(45) Date of Patent: Feb. 4, 2014

(54) MAGNETIC RESONANCE IMAGING

(75) Inventors: Tobias Kober, Lausanne (CH); Gunnar Krueger, Lausanne (CH); Delphine Ribes, Bern (CH)

(73) Assignees: Siemens Schweiz AG, Zurich (CH); Unversite de Lausanne, Lausanne (CH)

( * ) Notice: Subject to any disclaimer, the term of this patent is extended or adjusted under 35 U.S.C. 154(b) by 0 days.

(21) Appl. No.: 13/450,703

(22) Filed: Apr. 19, 2012

(65) Prior Publication Data
US 2012/0271146 A1 Oct. 25, 2012

(30) Foreign Application Priority Data

Apr. 19, 2011 (EP) .................................... 11163001

(51) Int. Cl.
*A61B 5/055* (2006.01)
(52) U.S. Cl.
USPC .......................................... 600/410; 600/407
(58) Field of Classification Search
USPC .................... 600/407, 410; 324/318–320
See application file for complete search history.

(56) References Cited

U.S. PATENT DOCUMENTS

2006/0064004 A1* 3/2006 Machida ....................... 600/410
2008/0119721 A1 5/2008 Kimura et al.

OTHER PUBLICATIONS

European Search Report dated Sep. 13, 2011.
Koen Van Leemput, et al., "Automated Model-Based Tissue Classification on MR Images of the Brain," IEEE Transactions on Medical Imaging, Oct. 10, 1999, pp. 897-908, vol. 18, No. 10, Piscataway, NJ, USA.

* cited by examiner

*Primary Examiner* — Peter Luong
(74) *Attorney, Agent, or Firm* — Laurence A. Greenberg; Werner H. Stemer; Ralph E. Locher

(57) ABSTRACT

A method removes a part representing non-brain tissue of the MR brain image. For each generated magnetic field gradient, acquiring a current signal respectively at a first time of echo $TE_1$ after an excitation radio frequency pulse and at a second time of echo $TE_2$ after the radio frequency pulse. The MR brain image of an internal structure of the target. The first time of echo $TE_1$ and the second time of echo $TE_2$ are adjusted for correlating time of echo difference $\Delta TE=TE_2-TE_1$ with a fat and water mutual resonance frequency difference $\delta$, and in that fat and water information encoded in the current signal resulting from the correlation of the second and first time of echo difference $\Delta TE$ with the fat and water mutual resonance frequency difference is used as an additional input source into a multispectral analysis method for removing the part.

7 Claims, 3 Drawing Sheets

MAGNETIC RESONANCE IMAGING

CROSS-REFERENCE TO RELATED APPLICATION

This application claims the priority, under 35 U.S.C. §119, of European application EP 11163001, filed Apr. 19, 2011; the prior application is herewith incorporated by reference in its entirety.

BACKGROUND OF THE INVENTION

Field of the Invention

The invention relates to a method and a device for the removal of non-cerebral tissue in magnetic resonance (MR) imaging. In particular, the invention relates to a method and a device for removing image parts representing non-brain tissues, such as skull, scalp, veins or meninges, from a MR neuro-image.

In order to obtain images using the technique of MR imaging, the subject to be imaged is placed in a strong static magnetic field, which forces the hydrogen nuclear magnetic moments associated with the subject hydrogen nuclear spins to adopt an orientation parallel or anti-parallel with respect to the static magnetic field. The spin axes are not exactly aligned with the static magnetic field, but they precess around a direction axis of the static magnetic field with a characteristic frequency, giving rise to a net magnetization in the direction of the static magnetic field. In order to stimulate a signal from the hydrogen nuclei, a pulse of radio frequency energy can be applied to the subject at the aforementioned characteristic frequency, called Larmor frequency, which is for one type of nuclei proportional to the flux density of the magnetic field. The radio frequency energy associated with this pulse disturbs the net magnetization from its equilibrium, rotating it away from the static magnetic field with an angle, called flip angle, which depends on the strength and duration of the magnetic component of the electromagnetic radio frequency radiation. Consequently, the net magnetization begins to precess around the static magnetic field main axis, its transverse component inducing an electromotive force in a receiver coil according to Faraday's law of magnetic induction. This electromotive force gives rise to an induced signal that is then at the basis of MR image reconstruction. The magnitude of this induced signal depends, among other factors, on the number of nuclei that produce the magnetization, on their relaxation times, i.e. the time needed by the net magnetization to return to its equilibrium state along the axis of the strong magnetic field. Other factors include the so called spin preparation. In order to optimize a diagnostic value of the signal, different combinations of one or more radio frequency pulses have been proposed, while taking into account some parameters like a repetition time of the pulse, its echo time, the flip angle, its bandwidth, etc.

The time required for a substance to become magnetized after having been placed in a magnetic field or the time required for the substance to regain longitudinal magnetization following the radiofrequency pulse is usually called the longitudinal relaxation time $T1$ (also called spin-lattice relaxation). The longitudinal relaxation time $T1$ is in particular determined by thermal interactions between resonating protons and other protons and other magnetic nuclei in the environment submitted to the magnetic field. The longitudinal relaxation time $T1$ depends in particular on the relationship between the natural vibrational frequencies of the substance and the Larmor frequency. Similarly, a transverse relaxation time $T2$ (also called spin-spin relaxation) describes the interaction between neighbouring nuclei with identical precessional frequencies having different magnetic quantum states, and represents a measure of how long a transverse magnetization lasts following the radiofrequency pulse. The transverse relaxation time $T2$ characterizes thus the exponential decay of the induced signal resulting from the decline of coherence of the spin precession.

Each tissue of the human body is thus characterized by an own longitudinal relaxation time $T1$ and an own transverse relaxation time $T2$. Numerous studies used $T1$ weighted protocols, i.e. protocols giving rise to images where most of the contrast of the tissues is due to differences in the values of the longitudinal relaxation time $T1$, for imaging soft tissues, and in particular the brain, since the $T1$ weighted protocols generally offer a good contrast between the tissues forming the brain, like grey of white cerebral matter. Moreover, the evolution of high-resolution MR imaging of the last decades enabled advanced post-processing of brain images, enhancing the contrast between the tissues forming the brain. Brain contrast is for example crucial in morphometry, since quantitative measures are derived from the image data to determine the volume of certain brain tissues like grey or white cerebral matter, for supporting then diagnostic decisions and facilitating follow-up comparisons.

Unfortunately, one major problem in MR neuro-imaging is to obtain a good contrast for discriminating brain tissues from non-brain tissues like the skull. Often, the parts of the image representing non-brain tissues have to be erased before such an advanced image post-processing can be conducted. This process, usually called skull-stripping, is hampered by very similar image intensities of wanted and unwanted tissues, possibly leading to the elimination of too much or too little non-brain tissue, which can bias the final outcome of the following post-processing, and at worst, falsely influence the diagnostic decision.

Different methods involving various skull-stripping algorithms have been used for differentiating brain from non-brain tissues. These methods can be separated into two groups.

The first group includes methods based exclusively on $T1$ weighted protocols. These methods are for example:

a. the Brain Surface Extractor (BSE) [Shattuck et al., NeuroImage 13, 856 (2001)] which uses a combination of anisotropic diffusion filtering, Marr-Hildreth edge detector and morphological operators to separate brain and non-brain tissue;

b. the Watershed algorithm (WAT) [Hahn and Peitgen, MICCAI 2000, 134 (2000)]: an intensity-based approach relying on a 3D algorithm with pre-flooding performed on the intensity inverted image, selecting the basin to represent the brain;

c. the Brain Extraction Tool (BET) [Smith, Human Brain Mapping 17, 143 (2002)] which deforms a mask which is constraints on surface smoothness and voxel intensities in the vicinity to the surface position;

d. the Hybrid Watershed Algorithm (HWA) [Ségonne et al., NeuroImage 22, 1060 (2004)]: a hybrid approach combining watershed algorithm and deformable model, where the latter adds atlas based shape constraints in order to guarantee anatomically meaningful brain mask;

e. Suresh et al. [Suresh et al., NeuroImage 49, 225 (2010)] uses intensity thresholding followed by removal of narrow connections using graph cut segmentation theory to remove non brain tissue; and f. Keihaninejad et al. [Keihaninejad et al., 9th European Congress on Epileptology 51, 6 (2010)] extract the intracranial volume using posterior probability maps extracted using SPM5 and apply a specific threshold to keep only brain tissues.

The second group includes methods based on multispectral analysis. One of these methods has been developed by Van Leemput et al. [Van Leemput et al., IEEE Transactions on Medical Imaging 18, 897 (1999)]. They propose a framework to automatically classify brain tissue using multispectral acquisitions as T1 weighted, T2 weighted and proton density.

Unfortunately, the above-mentioned methods are not yet optimal, and there is still a need for improving the outcome of the skull-stripping procedure.

SUMMARY OF THE INVENTION

It is therefore an objective of the present invention to provide a method for removal of non-brain tissue of a MR head image before any advanced post processing technique in order to enable accurate measurement of brain structures and thus secure MR imaging diagnosis. Indeed, the improvement of skull-stripping methods is of vital interest for all advanced brain post-processing techniques.

The objective is achieved according to the present invention with respect to the method by a method for removing at least one part of a MR brain image, preferentially prior to post-processing of the MR brain image, the part representing non-brain tissue of the MR brain image and being in particular one or more pixels of the image. The method includes the steps of:
a) generating a static magnetic field capable of aligning moments of nuclei of a target to be imaged with a direction parallel with the static magnetic field, i.e. the static magnetic field is capable of aligning with it individual magnetic moment of spins of the target;
b) generating at least one excitation radio frequency pulse capable of exciting atom nuclei of the target being magnetized by the static magnetic field, and capable of deflecting the moments of nuclei from the direction of the static magnetic field;
c) generating for a first and a second predefined time period at least a first and a second magnetic field gradient, each capable of magnetizing the atom nuclei of the target and each designed for determining positional or spatial information of the excited atom nuclei of the target, the first and the second magnetic field gradient being oppositely directed magnetic field gradients so as to find out chemical spectral information of the target, the first and the second magnetic field gradient being notably generated temporally the one after the other one, and in particular, each of the first and second magnetic field gradient being a phase and frequency-encoding magnetic field gradient;
d) for each generated magnetic field gradient, i.e. respectively for the first and the second magnetic field gradient, acquiring a current signal, respectively at a first time of echo $TE_1$ (or time of first echo) after the excitation radio frequency pulse and at a second time of echo $TE_2$ (or time of second echo) after the excitation radio frequency pulse, by at least one induction coil, in particular by arrays of induction coils, designed for surrounding the target and capable of generating the current signal from the deflection of the nuclei moments according to induction;
e) reconstructing the MR brain image of an internal structure of the target from the current signal by computational processing of the current signal; and
f) the first time of echo $TE_1$ and the second time of echo $TE_2$ are adjusted for correlating a second and first time of echo difference $TE_2-TE_1$ with a fat and water mutual resonance frequency difference $\delta$, and in that a fat and a water information encoded in the current signal and resulting from the correlation of the second and first time of echo difference $TE_2-TE_1$ with the fat and water mutual resonance frequency difference is used as additional input source into a multispectral analysis method capable of automatically classifying brain tissue from multispectral acquisitions, for removing the at least one part representing non-brain tissue, and in order to improve the reconstruction of the MR brain image.

The invention provides thus additional image information, notably from separated fat and water signal image, without considerably prolonging the scan time or impeding the quality of the "normal" image contrast (the water and/or fat combined image). The multispectral analysis method contains in particular a data treatment by a multispectral skull-stripping algorithm (i.e. an algorithm using several image contrasts), yielding better target imaging results compared to normal MR imaging. Other aspects, inventive features, and advantages of the present invention will become apparent in the non-limiting detailed description set forth below.

The precession of the nuclei moments around the direction of the static magnetic field is detected by induction coils that are placed outside the target for inducing the current signal, which might be then subjected to Fourier transformation for studying its spectrum. In particular, the current signal is digitally sampled in the Fourier space (k-space) for generating the MR brain image. Preferentially, the radio frequency pulse is followed by a sampling of a certain number of data points in k-space from the current signal at the time of echo $TE_1$ after the radio frequency pulse of excitation. These points are notably selected using the phase- and frequency-encoding first magnetic field gradients. By applying an opposite phase- and frequency-encoding magnetic field gradient, i.e. the second magnetic field gradient, after the sampling of the data points, a second echo is induced, and can be acquired and sampled via the current signal at the time of the second echo $TE_2$.

The fat and water information encoded in the induced current signal can be extracted from the current signal by the following way, known as the Dixon technique [Dixon W T, Radiology 153:1, 189, (1984)]. The chemical shift $\delta$ of resonance signals of fat and water in body tissues relative to each other, or in other words their mutual resonance frequency difference, is $\delta=3.4$ ppm, which would correspond to the difference of circa 68 Hz in approximately 0.5 Tesla magnetic field. At 3 Tesla, the change in frequency is $\Delta f=\delta\gamma B_0=434$ Hz, where $\gamma$ is the gyromagnetic ratio of protons in the target and $B_0$ the static magnetic field strength. By adjusting the echo times in an imaging sequence of the above described type so that their difference $TE_2-TE_1$ equals $k/(2\Delta f)$ (for $k=1, 3, 5, \ldots$), water and fat signals accumulate a phase difference of $k\pi$ radians between the first and the second echo. Thus, the phase difference amounts to $\phi=TE_1 \cdot \Delta f/(2\pi)$ radians at time $TE_1$ and $\phi+k\pi$ radians at time $TE_2$.

In particular, if A is the complex image generated from data sampled at the time of echo $TE_1$ from the acquired current signal and B the complex image generated from data sampled at the time of echo $TE_2$ from the acquired current signal, then a fat (F) and water (W) information comprised in the acquired current signal is encoded as follows:

$$A = W \cdot e^{i\phi} + F \cdot e^{i\phi} = e^{i\phi} \cdot (W+F) \quad \text{(I)}$$

and $$B = W \cdot e^{i\phi} + F \cdot e^{i(\phi+\pi)} = e^{i\phi} \cdot (W-F) \quad \text{(II)}$$

Consequently, the extraction of the fat and water information from the complex images A and B gives rise to a water-only and fat-only image respectively calculated as follows:

$$W = I\tfrac{1}{2} \cdot (A+B)I \qquad (III)$$

and $$F = I\tfrac{1}{2} \cdot (A-B)I \qquad (IV),$$

where the resulting water-only image W resembles traditional image contrast obtained in MR imaging, whereas the fat-only image F depicts the fat in the tissue around the skull as well as inferior and anterior of the brain. Consequently, the method according to the invention is able to construct a water-only and fat-only image from the fat and water information encoded in the current signal. Advantageously, non-brain tissue around vessels is well depicted in the fat-only images, which is in particular used by the method according to the invention for skull-stripping purposes.

Indeed, each fat-only image, and/or respectively, each water-only image, is preferentially used for extracting data related to fat spatial position in the target, and/or respectively data related to water spatial position in the target, the data being then inputted as the additional input source into a multispectral skull-stripping algorithm of the multispectral analysis method such as for example the method presented in Van Leemput et al. [Van Leemput et al., IEEE Transactions on Medical Imaging 18, 897 (1999)]. In particular, the multispectral skull-stripping algorithm is able to provide from the data related to fat or water spatial position a digital image of the target comprising target tissues spatial position.

Advantageously, even in the case of a magnetization-prepared rapid gradient-echo (MP-RAGE) sequence, the acquisition of additional echoes according to the invention does not prolong an overall scan time. Optionally, a root-mean-square-combination C of data sampled at the time of echo $TE_1$, A, and the data sampled at time of echo $TE_2$, B, can be calculated by $$C = \tfrac{1}{2} \cdot \mathrm{sqrt}(A^2 + B^2)$$

as described in van der Kouwe et al. [NeuroImage 40:2, 559 (2008)]. The so computed image contrast equals the standard image contrast, i.e. the contrast which would be achieved without employing the Dixon technique, and recovers probable signal losses due to increased sampling bandwidths.

Other features which are considered as characteristic for the invention are set forth in the appended claims.

Although the invention is illustrated and described herein as embodied in an improved magnetic resonance imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
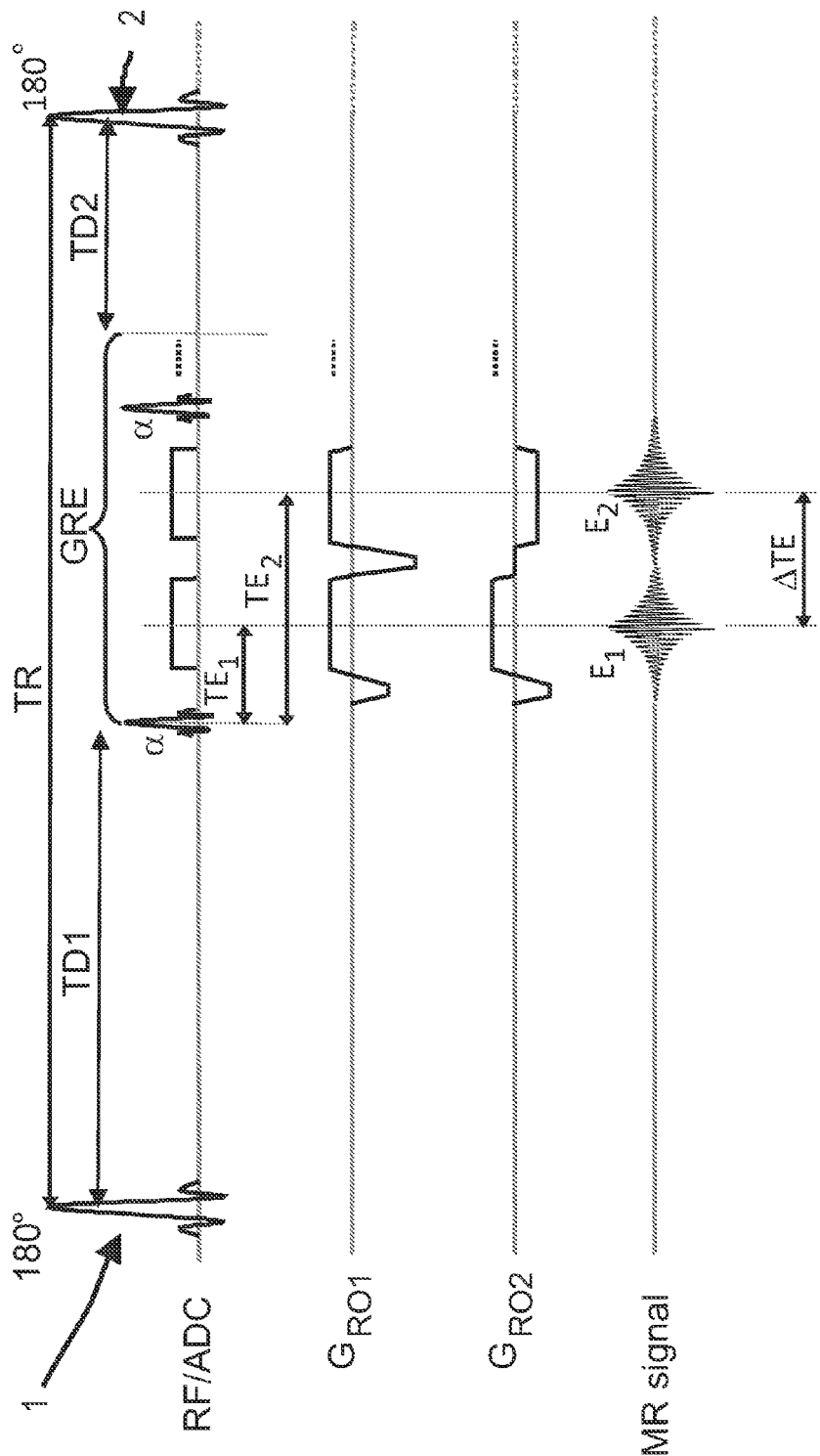
FIG. 1 is a schematic illustration of a conventional double-echo MP-RAGE image sequence.

Referring now to the figures of the drawing in detail and first, particularly, to FIG. 1 thereof, there is shown a preferred sequence of double-echo MP-RAGE for imaging a target according to the invention. The MP-RAGE sequence is chosen as an example since it is widely used to obtain T1-weighted image contrast. Other sequences might be used such as T1-weighted gradient echo (FLASH) or spin-echo-based sequences. The case of MP-RAGE depicted here shows an inversion radio frequency pulse 1 followed after a first delay time TD1 by a gradient echo readout train GRE performed through a period of time determined in function of a number of double-echo acquisitions to be performed. At the end of the period of time, the gradient echo readout GRE is succeeded by a second delay time TD2 which separates the end of the gradient echo readout GRE from the next inversion radio-frequency pulse 2. The first delay time TD1, the gradient echo readout GRE, and the second delay time form a block that is consecutively repeated, starting at each next inversion radio-frequency pulse, until k-space is fully sampled. The time between the two successive inversion radio-frequency pulses is characterized by the repetition time TR. Within the gradient echo readout train GRE, N double-echo acquisitions are performed. Each double-echo acquisition includes a generation of an excitation radio frequency pulse α which is in particular a low-flip-angle excitation pulse, and a sampling of data during a gradient echo which is achieved by dephasing the spins with at least one readout gradient that follows the excitation radio frequency pulse α. After the excitation radio frequency pulse α, in particular the low-flip-angle excitation pulse, two echoes are formed using in particular either a monopolar readout gradient scheme $G_{RO1}$ or a bipolar gradient scheme $G_{RO2}$. Pursuant to the configured readout gradients, two echoes, respectively an in-phase echo $E_1$ and an opposed-phase echo $E_2$, are formed at specific echo times $TE_1$ and $TE_2$, where $TE_1$, respectively $TE_2$, is an amount of time separating each excitation radio frequency pulse a from the middle (half the moment) of a first and respectively of a second magnetic field gradient, i.e. the monopolar or bipolar gradient represented by the readout gradient scheme $G_{RO1}$ or $G_{RO2}$. To obtain in-phase and opposed phase fat and water signals, $TE_1$ and $TE_2$, and thus the readout gradients, have to be adjusted as described previously by correlating the second and first time of echo difference $\Delta TE = TE_2 - TE_1$ with a fat and water mutual resonance frequency difference δ.

Figure 2:
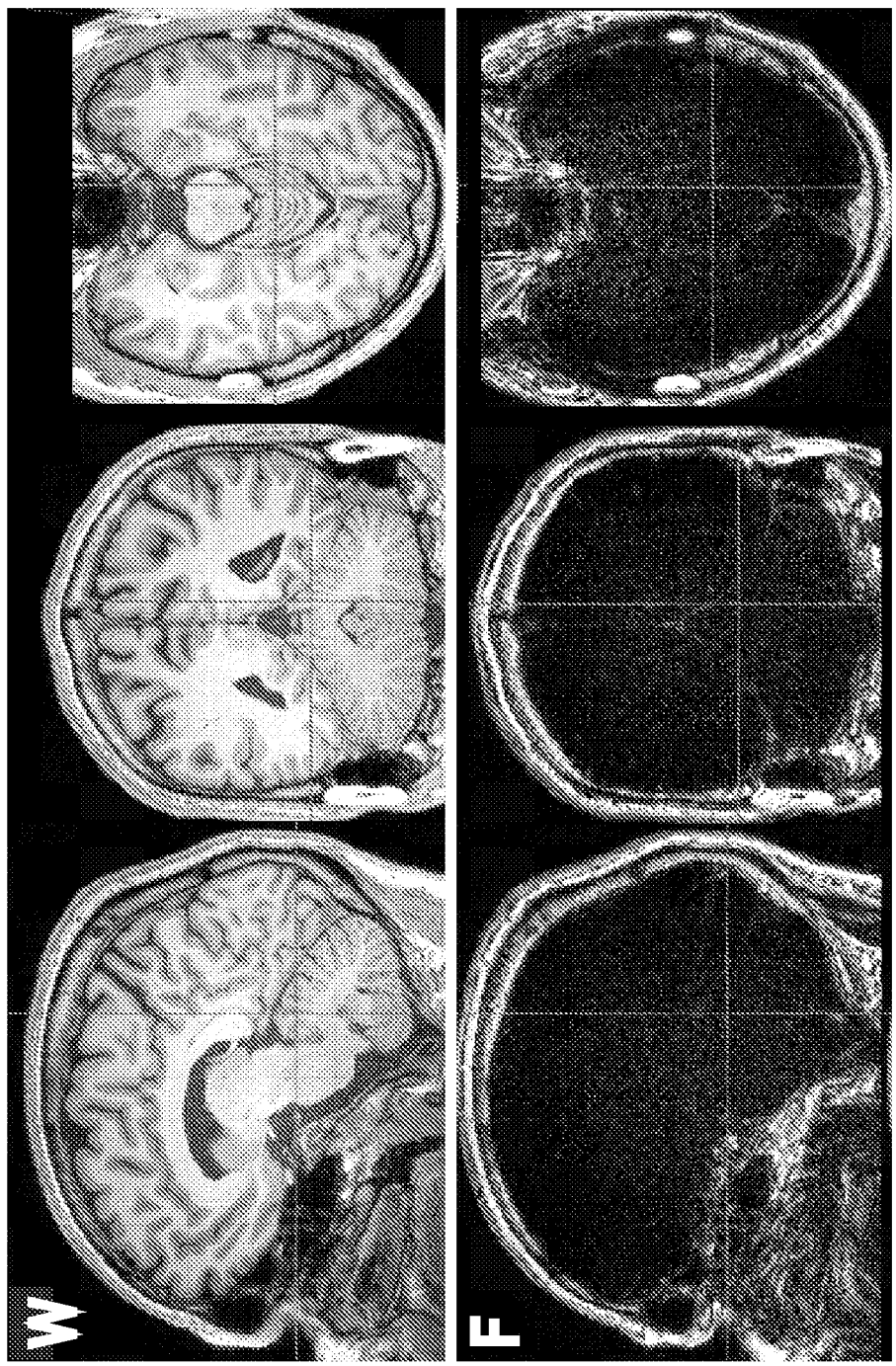
FIG. 2 is an illustration of exemplary fat-only (F) and water-only (W) images obtained according to the invention.

FIG. 2 illustrates water-only images W and fat-only images F acquired according to Dixon technique, from which additional image information which improves skull-stripping results is extracted according to the invention. Such images are in particular used as additional input source into a multispectral analysis method according to the present invention. Indeed, the multispectral skull-stripping algorithm is able to extract data related to fat spatial position in the target and/or data related to water spatial position in the target arising notably from differences between the water-only W and the fat-only F images, and to use it as complementary information, especially for the skull-tissue boundary regions.

Figure 3A:
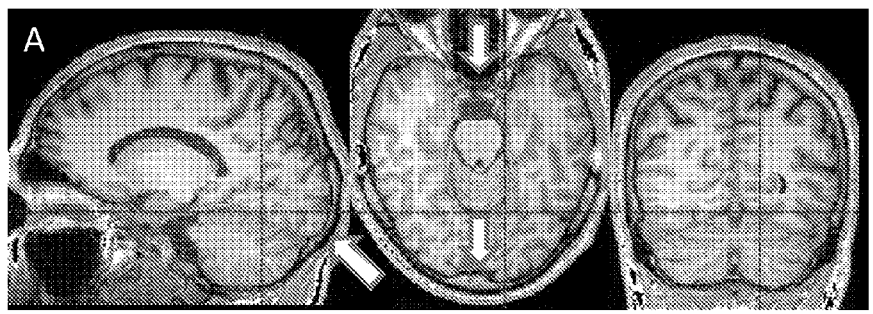
FIGS. 3A-3C are illustrations of examples of skull-stripping results obtained by MR imaging of a target according to the invention.
Figure 3B:
Figure 3C:
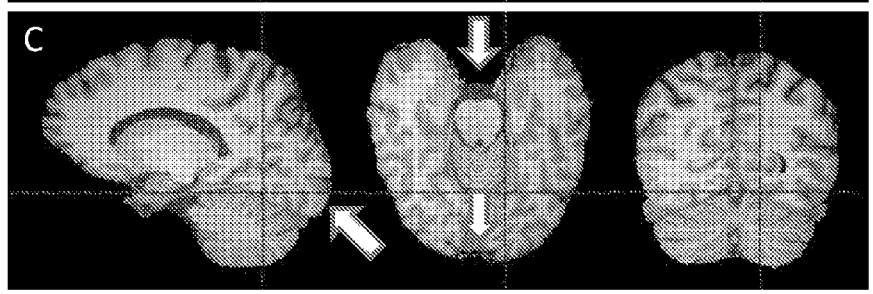

FIGS. 3A-3C exemplify the differences in the skull-stripping results obtained by a multispectral skull-stripping algorithm with or without applying the method according to the invention. Indeed, FIGS. 3A-3C present different examples of skull-stripping results obtained by MR imaging of a target, wherein FIG. 3A shows a fat and water combined image of the target, FIG. 3B shows the state of the art skull-stripping results (i.e. only FIG. 3A is used for skull-stripping) of the target, and FIG. 3C shows images obtained for the same target by applying the claimed invention. Using the formulas I-IV, data of the two echoes $E_1$ and $E_2$ are combined to obtain a common T1-weighted contrast with optimized SNR. Using this alone as an input for the skull-stripping algorithm, suboptimal results are achieved (see FIG. 3B). Exploiting also the fat image as complementary information in the algorithm ameliorates the outcome significantly (see FIG. 3C). Arrows indicate areas of better separation, the invention particularly improves results in inferior-posterior regions.

Finally, in contrast to state of the art techniques, the present invention features the parallel acquisition of two image volumes; in a post-processing step, a standard T1-weighted contrast and an additional fat contrast depicting mainly undesired tissues is obtained. Both are subsequently used in a general multispectral analysis. Hence, the information available to the multispectral algorithm is augmented by additional information about the location of undesired, i.e. non-brain, parts of the image. The method according to the invention presents thus the following advantages compared to conventional skull-stripping procedures:

a. it significantly improves the outcome of the skull-stripping procedure at negligible cost in terms of scan/processing time;
b. compared to a mono-spectral (i.e. only one image) input, the multispectral skull-stripping algorithm can make use of the complementary information especially in the skull-tissue boundary regions;
c. no prolongation of the overall scan time by employing a MPRAGE sequence;
d. intrinsic co-registration of the images yielded by the different echoes;
e. simple computation of the water and fat image; and
f. no significant prolongation of post-processing times.

The invention claimed is:

1. A method for removing at least one part of a MR brain image, the part representing non-brain tissue of the MR brain image, which method comprises the steps of:
generating a static magnetic field capable of aligning moments of nuclei of a target to be imaged with a direction parallel with the static magnetic field magnetic;
generating at least one excitation radio frequency pulse (a) capable of exciting atom nuclei of the target being magnetized by the static magnetic field, and capable of deflecting the moments of nuclei from a direction of the static magnetic field;
generating for a first and a second predefined time period at least a first and a second magnetic field gradient, each capable of magnetizing the atom nuclei of the target and each designed for determining positional or spatial information of an excited atom nuclei of the target, the first and the second magnetic field gradient being oppositely directed magnetic field gradients;
acquiring a current signal for each generated magnetic field gradient, respectively at a first time of echo $TE_1$ after the excitation radio frequency pulse ($\alpha$) and at a second time of echo $TE_2$ after the excitation radio frequency pulse ($\alpha$), by means of at least one induction coil designed for surrounding the target and capable of generating the current signal from a deflection of the moments of nuclei according to induction;
reconstructing the MR brain image of an internal structure of the target from the current signal by means of computational processing of the current signal; and
adjusting the first time of echo $TE_1$ and the second time of echo $TE_2$ for correlating a second and first time of echo difference $\Delta TE = TE_2 - TE_1$ with a fat and water mutual resonance frequency difference $\delta$; and
using fat and water information encoded in the current signal and resulting from a correlation of the second and first time of echo difference $\Delta TE$ with a fat and water mutual resonance frequency difference as an additional input source into a multispectral analysis method for removing the at least one part representing the non-brain tissue.

2. The method according to claim 1, which further comprises performing the multispectral analysis method, the multispectral analysis method including a data treatment by a multispectral skull-stripping algorithm.

3. The method according to claim 1, which further comprises constructing a water-only and fat-only image from the fat and water information encoded in the current signal.

4. The method according to claim 3, which further comprises using each fat-only image for extracting data related to a fat spatial position in the target.

5. The method according to claim 3, which further comprises using each water-only image for extracting data related to a water spatial position in the target.

6. The method according to claim 4, which further comprises inputting the data as the additional input source into the multispectral skull-stripping algorithm.

7. The method according to claim 1, which further comprises performing the multispectral analysis method.

* * * * *